United States Patent
Turng et al.

(10) Patent No.: US 7,998,380 B2
(45) Date of Patent: Aug. 16, 2011

(54) METHOD OF FABRICATING A TISSUE ENGINEERING SCAFFOLD

(75) Inventors: Lih-Sheng Turng, Madison, WI (US); Adam J. Kramschuster, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 11/777,555

(22) Filed: Jul. 13, 2007

(65) Prior Publication Data

US 2009/0017094 A1    Jan. 15, 2009

(51) Int. Cl.
*B29C 67/20* (2006.01)

(52) U.S. Cl. .... 264/49; 264/413; 264/36.11; 264/37.15; 264/48; 264/367; 264/351; 264/86; 264/288.8; 264/916; 264/645; 264/513; 264/537; 264/297.2

(58) Field of Classification Search ................. 264/413, 264/36.11, 37.15, 48, 637, 651, 86, 288.8, 264/916, 645, 513, 537, 297.2

See application file for complete search history.

(56) References Cited

U.S. PATENT DOCUMENTS

| | | | |
|---|---|---|---|
| 3,730,918 A * | 5/1973 | Teti et al. ..................... | 521/64 |
| 5,679,723 A | 10/1997 | Cooper et al. | |
| 6,103,255 A * | 8/2000 | Levene et al. ................. | 424/426 |
| 6,306,424 B1 | 10/2001 | Vyakarnam et al. | |
| 6,322,347 B1 * | 11/2001 | Xu ............................... | 425/376.1 |
| 6,333,029 B1 | 12/2001 | Vyakarnam et al. | |
| 6,365,149 B2 | 4/2002 | Vyakarnam et al. | |
| 6,534,084 B1 | 3/2003 | Vyakarnam et al. | |
| 6,626,950 B2 | 9/2003 | Brown et al. | |
| 6,692,761 B2 | 2/2004 | Mahmood et al. | |
| 6,746,685 B2 | 6/2004 | Williams | |
| 6,773,713 B2 | 8/2004 | Bonassar et al. | |
| 6,852,330 B2 | 2/2005 | Bowman et al. | |
| 6,884,428 B2 | 4/2005 | Binette et al. | |
| 7,112,417 B2 | 9/2006 | Vyakarnam et al. | |
| 2004/0010048 A1 * | 1/2004 | Evans et al. ..................... | 521/50 |
| 2004/0026811 A1 * | 2/2004 | Murphy et al. .................. | 264/41 |
| 2005/0107868 A1 * | 5/2005 | Nakayama et al. .......... | 623/1.39 |
| 2005/0165475 A1 | 7/2005 | Noh | |
| 2006/0002978 A1 * | 1/2006 | Shea et al. ..................... | 424/426 |
| 2006/0083771 A1 | 4/2006 | Yamamoto et al. | |
| 2006/0153814 A1 | 7/2006 | Liao et al. | |

OTHER PUBLICATIONS

Shao, Xin Xin, et al., Evaluation of a hybrid scaffold/cell construct in repair of high-load-bearing osteochondral defects in rabbits, Biomaterials 27 (2006) pp. 1071-1080, Elsevier, Cambridge, MA.
Nho, Shane J. et al., Patellofemoral Osteochondral Autologous Transfer, Techniques in Knee Surgery 5(2), pp. 134-137, 2006, Lippincott Williams & Wilkins, Philadephia, PA.
Mikos, Antonios G., et al., Preparation and characterization of poly (L-lactic acid) foams, Polymer, vol. 35 No. 5, 1994 pp. 1068-1077, Butterworth-Heinemann Ltd., Burlington, MA.

(Continued)

*Primary Examiner* — Christina Johnson
*Assistant Examiner* — Stella Yi
(74) *Attorney, Agent, or Firm* — Boyle Fredrickson, s.c.

(57) ABSTRACT

A method of fabricating a highly porous structure is provided. The method includes the step of compounding a biodegradable polymer, a water-soluble polymer and a porogen to form a composite blend. A foaming agent is dissolved into the composite blend and the composite blend is injected into a mold so as to form the structure. Thereafter, the structure is removed from the mold and leached in a fluid.

20 Claims, 1 Drawing Sheet

OTHER PUBLICATIONS

Mooney, David J., et al., Novel approach to fabricate porous sponges of poly (D,L-lactic-co-glycolic acid) without the use of organic solvents, Biomaterials 17 (1996) 1417-1422, Elsevier, Cambridge, MA.

Nam, Yoon Sung, et al., A novel fabrication method of macroporous biodegradable polymer scaffolds using gas foaming salt as a porogen additive, Journal of Biomedical Materials Research (Applied Biomaterials) 53:1-7, 2000 John Wiley & Sons, Inc., Hoboken, NJ.

Harris, Leatrese, et al., Open Pore Biodegradable matrices formed with gas foaming, Journal of Biomedical Materials Research, vol. 42, No. 3, Dec. 5 1998. pp. 396-402, 2000, John Wiley & Sons, Inc., Hoboken, NJ.

Washburn, Newell R., et al., Co-extrusion of biocompatible polymers for scaffolds with co-continuous morphology, Journal of Biomedical Materials Research, vol. 60, No. 1, pp. 20-29, 2002, John Wiley & Sons, Inc., Hoboken, NJ.

Wang, Xiaoxi, et al., Solvent Free Fabrication of Biodegradable Porous Polymers, Proceedings of Imece04, pp. 595-602, 2204, American Society of Mechanical Engineers, New York, New York.

Wu, Linbo, et al., a "room-temperature" injection molding/particulate leaching approach for fabrication of biodegradable three-dimensional porous scaffolds, Biomaterials, 27 (2006) pp. 185-191, Elsevier, Cambridge, MA.

Leicher, S., et al., MuCell® technology for injection molding: A processing method for polyether-urethane scaffolds, Journal of Materials Science, 40 (17): 4613-4618, 2005, Springer Science + Business Media, Inc., New York, New York.

Reignier, Joel, et al., Preparation of Interconnected Polycaprolactone Porous Scaffolds by a Combination Polymer and Salt Particulate Leaching, Proceedings of ANTEC 2005, pp. 2550-2554, Society of Plastics Engineers, Brookfield, CT.

Neves, Nuno M., et al., The morphology, mechanical properties and ageing behavior of porous injection molded starch-based blends for tissue engineering scaffolding, Materials Science & Engineering, C 25 (2205) pp. 195-200, Elsevier, Cambridge, MA.

Haugen, H. et al., A Novel Processing Method for Injection-Molded Polyether-Urethane Scaffolds. Part 1: Processing, Journal of Biomedical Materials Research Part B—Applied Biomaterials, vol. 77B, No. 1 (Apr. 2006), pp. 65-72, Wiley-Liss, Div John Wiley & Sons Inc, Hoboken, NJ.

* cited by examiner

METHOD OF FABRICATING A TISSUE ENGINEERING SCAFFOLD

REFERENCE TO GOVERNMENT GRANT

This invention was made with United States government support awarded by the following agency: NSF 0544729. The United States has certain rights in this invention.

FIELD OF THE INVENTION

This invention relates generally to tissue engineering, and in particular, to a method for mass producing geometrically complex, highly porous and interconnected biodegradable structures for tissue engineering and drug delivery applications.

BACKGROUND AND SUMMARY OF THE INVENTION

Tissue Engineering is a multidisciplinary field encompassing the principles of bioengineering, cell transplantation, and material science. The goal of tissue engineering is to develop tissue substitutes that may be used to restore, maintain, or improve the function of diseased or damaged human tissues. For example, it is contemplated to seed a man-made platform, called a scaffold, with donor cells and/or growth factors. The scaffolds may then be cultured and implanted in the human body to induce and direct the growth of new, healthy tissue. Similarly, scientists are trying to develop implantable, biodegradable devices that would act as drug delivery vessels.

In order to obtain proper tissue ingrowth and ensure desired nutrient/cell delivery using an implanted scaffold, the quality of the scaffold is essential. For example, for purposes of nutrient/cell delivery, pathways must be provided in the scaffold for the nutrients/cells. Consequently, the scaffold must be highly porous and the pores defined by the scaffold must be highly interconnected. However, it can be appreciated that by increasing the porosity of the scaffold, the mechanical properties of the scaffold will correspondingly decrease. Further, it highly desirable for the implanted scaffold to be fabricated from a material, such as a biodegradable polymer, that is gradually absorbed into the human body. By constructing the scaffold from a biodegradable material, it is ensured that only natural tissue remains in the body after a predetermined time period. For example, scaffolds may be fabricated from polylactic acid (PLA), a polyester which degrades within the body to form lactic acid, polyglycolic acid (PGA), polycaprolactone (PCL) or one of a plurality of natural materials such as proteic materials (collagen, fibrin) or polysaccharidic materials (chitosan, glycosaminoglycans). In addition, in drug delivery applications, it is highly desirable for the scaffold to provide a high surface area to volume ratio. Further, it is often desirable for the scaffold to degrade at a desired rate to properly time the release of the drug to be delivered.

In order for biodegradable tissue engineering scaffolds to be routinely used in the medical field, a manufacturing method must be developed to mass produce geometrically complex scaffolds without the use of organic solvents. While several such methods for fabricating scaffolds have been proposed and produced in the laboratory, most of these methods utilize organic solvents which could render the scaffolds unusable for their intended purposes. Further, these prior methods are not practical for mass producing such scaffolds. As such, attempts have been made to fabricate the scaffolds from microcellular injection molding. As is known, microcellular injection molding is an ideal method for manufacturing a high volume of lightweight, highly dimensionally stable foamed parts with complex geometry. However, the achievable porosity of approximately 30% when utilizing present microcellular injection methods for thermoplastic materials falls far below the required porosity for tissue engineering scaffolds, though the percentage of porosity is highly dependent on the type of tissue and mechanical properties required for the specific application.

Therefore, it is a primary object and feature of the present invention to provide a method for mass producing biodegradable structures for tissue engineering and drug delivery applications.

It is a further object and feature of the present invention to provide a method for producing geometrically complex, highly porous and interconnected biodegradable structures for tissue engineering and drug delivery applications.

It is a still further object and feature of the present invention to provide a method for producing biodegradable structures for tissue engineering and drug delivery applications that is simple and inexpensive.

In accordance with the present invention, a method of fabricating a highly porous structure is provided. The method includes the step of compounding a biodegradable polymer, a water-soluble polymer and a porogen to form a composite blend. The composite blend is injected into a mold and processed therein to generate the structure. The structure is then leached in a fluid for a time period.

The method may include the additional step of introducing a gas in a supercritical state into the composite blend prior to processing the mixture in the mold. It is contemplated that the gas be carbon dioxide, the porogen be sodium chloride, the biodegradable polymer be polylactide and the water-soluble polymer be polyvinyl alcohol. The method may include the additional steps of sieving the porogen to a particle size of less than 300 microns and introducing a foaming agent into the composite blend.

In accordance with a further aspect of the present invention, a method of fabricating a highly porous stricture is provided. The method includes the step of compounding a biodegradable polymer, a water-soluble polymer and a porogen to form a composite blend. A foaming agent is dissolved into the composite blend and the composite blend is injected into a mold to form the structure. Thereafter, the structure is leached in a fluid.

The step of dissolving a foaming agent into the composite blend includes the additional step of introducing a gas in a supercritical state into the composite blend and mixing the composite blend. It is contemplated the gas be carbon dioxide, the porogen be sodium chloride, the biodegradable polymer be polylactide and the water-soluble polymer be polyvinyl alcohol. The method may include the additional step of sieving the porogen to a particle size of less than 300 microns.

In accordance with a still further aspect of the present invention, a method of fabricating a highly porous structure is provided. The method includes the step of introducing a foaming agent into a compound that includes a biodegradable polymer, a water-soluble polymer and a porogen. The compound is processed in a mold to form the structure.

The method may include the steps of leaching the structure in a fluid. The step of introducing a foaming agent may include the additional steps of introducing a gas in a supercritical state into the compound and mixing the compound. It is contemplated that the gas be carbon dioxide, the porogen be sodium chloride, the biodegradable polymer be polylactide and the water-soluble polymer be polyvinyl alcohol. The porogen agent may be sieved to a particle size of less than 300 microns.

BRIEF DESCRIPTION OF THE DRAWINGS

The drawings furnished herewith illustrate a preferred construction of the present invention in which the above advantages and features are clearly disclosed as well as others which will be readily understood from the following description of the illustrated embodiment.

In the drawings.

DETAILED DESCRIPTION OF DRAWINGS

Figure 1:
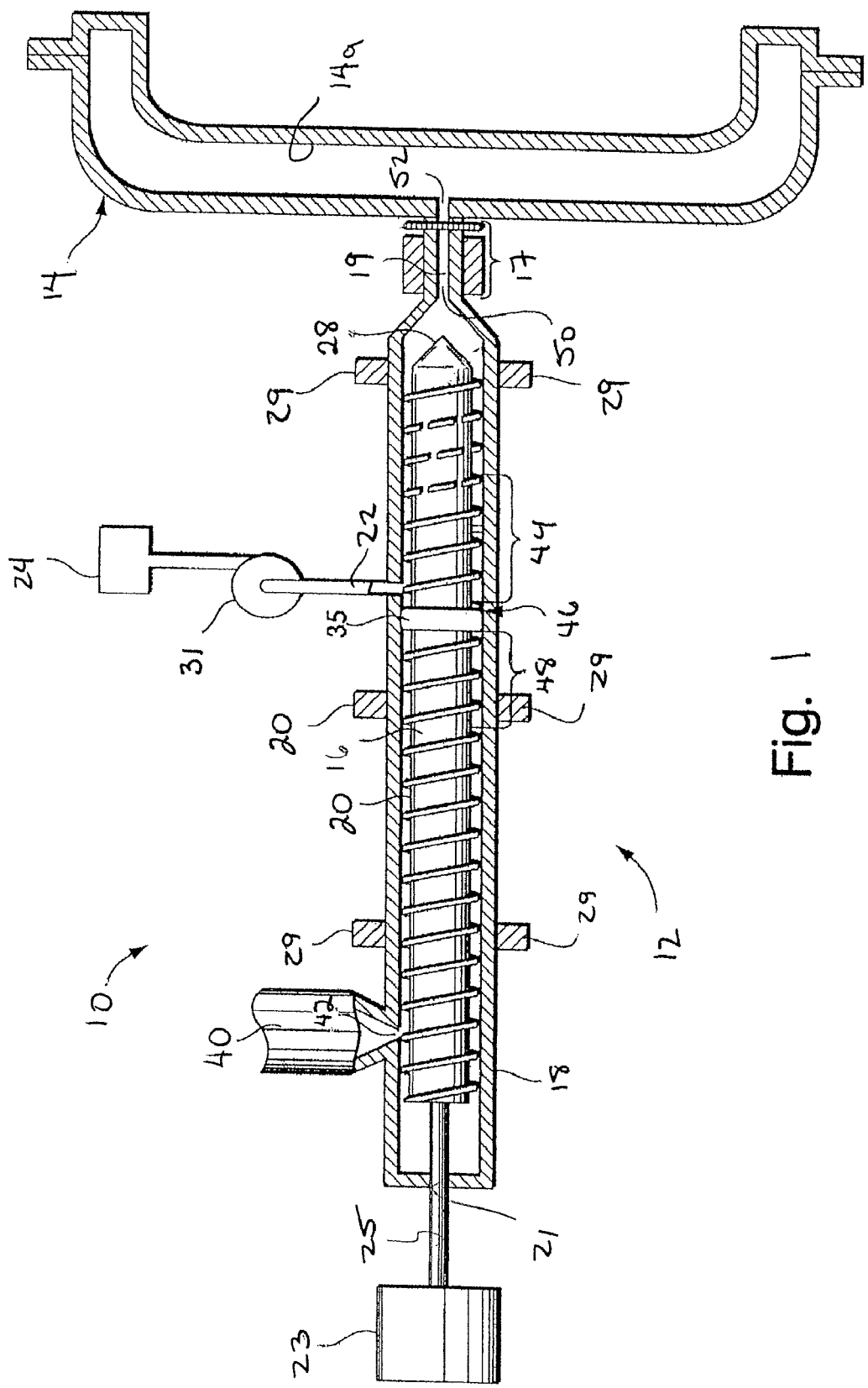
FIG. 1 is a schematic view of an injection molding machine for use in performing the methodology of the present invention.

Referring to FIG. 1, an injection molding machine for use in performing the methodology of the present invention is generally designated by the reference numeral 10. Injection molding machine 10 includes extruder 12 fluidly connected to mold 14. Screw 16 extends along a longitudinal axis and is rotatably supported within barrel 18 to convey polymeric material downstream within polymer processing space 20 toward mold 14. Barrel 18 is adapted to receive polymeric materials that are fluidic, or can form a fluid that subsequently hardens to form a conventional, or solid, polymeric article. Barrel 18 includes a first end fluidly connected to mold 14 through nucleating pathway 19 of nucleator 17 and a second, opposite end having aperture 21 extending therethrough. Drive motor 23 is operatively connected to screw 16 by drive shaft 25 extending through aperture 21 in second end of barrel 18. Drive motor 23 is operatively connected to a controller (not shown) for controlling rotational and axial movement of screw 16.

Injection molding machine 10 includes hopper 40 for receiving pelletized polymeric material therein. The polymeric material is delivered into polymer processing space 20 within barrel 18 through orifice 42. Polymer processing space 20 is defined by the outer surface of screw 16 and the inner surface of barrel 18. It is noted that the polymeric material may be a fluid pre-polymeric material injected through orifice 42 and polymerized within barrel 18 via, for example, an auxiliary polymerization agent. In connection with the present invention, it is important only that a fluid stream of polymeric material be established in the barrel 18.

Injection molding machine 10 further includes at least one foaming agent port 22 fluidly connecting foaming agent source 24 to polymer processing space 20 within barrel 18. As hereinafter described, it is intended for a foaming agent to be injected into the polymeric material within the polymer processing space 18 to form a polymer and foaming agent solution therein. Pressure and metering device 31 is provided between foaming agent source 24 and the at least one foaming agent port 22. Pressure and metering device 31 may be used to meter the foaming agent so as to control the amount of the foaming agent in the polymeric stream within barrel 18 and maintain the foaming agent at a desired level.

Although foaming agent port 22 may be located at any of a variety of locations along barrel 18, it is preferably located just upstream from mixing section 44 of screw 16 and from foaming agent receiving section 46 of screw 16 wherein screw 16 includes unbroken flights. Mixing section 44 is adapted for mixing the foaming agent and polymeric material to promote the formation of a single-phase solution of the polymeric material and the foaming agent within barrel 18.

A plurality of temperature control units 29 are positioned along barrel 18. For example, control units 29 can take any suitable form such as electrical heaters or the like. It is intended for control units 29 to heat a stream of pelletized or fluid polymeric material within barrel 18 to facilitate melting and/or cooling of the stream to control viscosity and, in some cases, the solubility of the foaming agent. Control units 29 can operate differently at different locations along barrel 18. For example, a first portion of control units 29 may heat the stream at one or more locations along barrel 18, while a second portion of the control units 29 may cool the stream at one or more different locations along barrel 18.

Injection molding machine 10 further includes restriction element 35 upstream of foaming agent port 22 and foaming agent receiving section 46 and downstream of a metering section 48 of screw 16 to maintain the polymeric material and foaming agent solution downstream of the restriction element at sufficient pressure throughout the injection process. Restriction element 35 is one example of an arrangement in which extruder 12 is constructed and arranged to maintain a solution of polymer and foaming agent within polymer processing space 20 between foaming agent port 22 and inlet 50 of nucleating pathway 19 at a relatively high pressure through an injection or ejection cycle, hereinafter described. Restriction element 35 can take any of a variety of forms known in the art for restricting the upstream flow of polymer material, such as a blister, a dam across the feed-section of the screw, a reverse screw flight, a valve or a ring check valve.

In order to form the biodegradable structure, it is contemplated to compound a porogen with a biodegradable polymer and a water-soluble polymer. More specifically, a porogen, such as sodium chloride (NaCl), is sieved to a particle size of 150 to 300 microns. NaCl, the biodegradable polymer, e.g., polylactide (PLA), and the water-soluble polymer, e.g., polyvinyl alcohol (PVOH), are compounded in a conventional manner, as with a twin screw extruder, to generate a plurality of extruded strands. It is contemplated to utilize other biodegradable polymers or water-soluble polymers without deviating from the scope of the present invention. In the present embodiment, the materials are compounded in a ratio of 60-vol % NaCl, 20-vol % PVOH, and 20-vol % PLA. However, it can be appreciated that other formulations are possible without deviating from the scope of the present invention. The extruded strands are cooled with compressed air and then pelletized. The pellets are deposited in hopper 40. Supercritical gas, e.g., carbon dioxide, is provided as the foaming agent source 24 to the injection molding machine 10. It is noted that other foaming agents, e.g., supercritical nitrogen, may be used without deviating from the scope of the present invention.

At the beginning of an injection cycle, screw 16 is axially positioned adjacent the first end of barrel 18 in an initial position. The pelletized polymeric material is delivered into polymer processing space 20 in barrel 18 through orifice 42 and screw 16 is rotated to urge the polymeric material downstream. Supercritical carbon dioxide is introduced into polymer processing space 20 through at least one foaming agent port 22 where it is mixed with the polymeric material via screw 16. Screw 16 maintains sufficient back pressure at all times to prevent premature foaming or the loss of pressure within extruder 12 which would allow the single phase solution to return to a two phase solution. The single-phase solution of the supercritical carbon dioxide and the polymeric material formed in extruder 12 has a very low viscosity which advantageously allows lower temperature molding, as well as, rapid filling of molds having close tolerances to form very thin molded parts. The polymeric material and foaming agent solution is accumulated in accumulation region 28 within barrel 18 downstream of screw 16.

Once a sufficient volume of the solution has accumulated in the accumulation region 28, screw 16 is moved in a downstream direction so as to inject the solution into nucleating pathway 19 through inlet 50 thereof. As the single-phase solution of polymeric material and foaming agent passes through nucleating pathway 19, the pressure drop in the nucleating pathway 19 causes the nucleation of the solution. The nucleated polymeric material is injected into the molding chamber of mold 14 through outlet 52 of nucleating pathway 19. After injection, screw 16 once again rotates to build up the polymeric material (and foaming agent) in the accumulation region 28 for the next injection.

The nucleated polymeric material received in the molding chamber of mold 14 begins to cool as soon as the nucleated polymeric material contacts inner surface 14a of mold 14. The molding chamber of mold 14 is filled with the nucleated polymeric material and the nucleated polymeric material solidifies into a part as it cools. After a sufficient time period has passed, the cooled part may now be ejected from mold 14. As is conventional, the size and shape of the part corresponds to the size and shape of the molding chamber of mold 14. Mold 14 is opened and the part is ejected therefrom. Once the part is ejected, mold 14 is closed and the process may be repeated.

The molding process heretofore described utilizes the highly controlled use of gas in its supercritical state to create micron-sized voids in thin wall molded parts. The voids are created or nucleated as a result of homogeneous nucleation that occurs when a single-phase solution of the polymeric material and the carbon dioxide passes through outlet 52 of nucleating pathway 19. With the correct equipment configuration, mold design, and processing conditions these microcellular voids are relatively uniform in size and distribution. However, as previously noted, the maximum achievable porosity of the part is approximately 30%.

In order to increase the porosity of the part, the NaCl and the PVOH within the part are leached therefrom. By way of example, the part is deposited in a volume of filtered, deionized water. Thereafter, the part is leached for approximately 72 hours using a hot plate and stir bar, changing the water every 24 hours. Once leached, it has been found that a continuous network of fully interconnected pores has been created within the part. More specifically, the part has a porosity of at least 75% that may be used for tissue engineering applications.

Various modes of carrying out the invention are contemplated as being within the scope of the following claims particularly pointing and distinctly claiming the subject matter that is regarded as the invention.

We claim:

1. A method of fabricating a highly porous structure, comprising the steps of:
    blending a biodegradable polymer, a water-soluble polymer and a porogen to form a composite blend;
    introducing a gas in a supercritical state into composite blend;
    mixing the gas into the composite blend to a form a single-phase solution prior to injecting the composite blend into the mold;
    injecting the single-phase solution into a mold;
    processing the single-phase solution in the mold to generate the structure; and
    leaching the structure in a fluid for a time period such that the water-soluble polymer is extracted from the structure.

2. The method of claim 1 wherein the gas is carbon dioxide.
3. The method of claim 1 wherein the porogen is sodium chloride.
4. The method of claim 1 wherein the biodegradable polymer is polylactide.
5. The method of claim 1 wherein the water-soluble polymer is polyvinyl alcohol.
6. The method of claim 1 comprising the additional step of sieving the porogen to a particle size of less than 300 microns.
7. A method of fabricating a highly porous structure, comprising the steps of:
    compounding a biodegradable polymer, a water-soluble polymer and a porogen to form a composite blend;
    dissolving a foaming agent into the composite blend;
    mixing the foaming agent and composite blend to form a single-phase solution;
    injecting the single-phase solution into a mold to form the structure; and
    leaching the structure in a fluid such that the water-soluble polymer is extracted from the structure.
8. The method of claim 7 wherein the step of dissolving a foaming agent into the composite blend includes the additional step of introducing a gas in a supercritical state into the composite blend.
9. The method of claim 8 wherein the gas is carbon dioxide.
10. The method of claim 7 wherein the porogen is sodium chloride.
11. The method of claim 7 wherein the biodegradable polymer is polylactide.
12. The method of claim 7 wherein the water-soluble polymer is polyvinyl alcohol.
13. The method of claim 7 comprising the additional step of sieving the porogen to a particle size of less than 300 microns.
14. A method of fabricating a highly porous structure, comprising the steps of:
    introducing a foaming agent into a compound including a biodegradable polymer, a water-soluble polymer and a porogen;
    mixing the foaming agent and the compound within a barrel of an injection molding machine;
    injecting the mixture of the foaming agent and the compound into a mold under pressure;
    processing the compound in the mold to form the structure; and
    leaching the structure in a fluid such that the water-soluble polymer is extracted from the structure.
15. The method of claim 14 wherein the step of introducing a foaming agent includes the additional step of:
    introducing a gas in a supercritical state into the compound.
16. The method of claim 15 wherein the gas is carbon dioxide.
17. The method of claim 14 wherein the porogen is sodium chloride.
18. The method of claim 14 wherein the biodegradable polymer is polylactide.
19. The method of claim 14 wherein the water-soluble polymer is polyvinyl alcohol.
20. The method of claim 14 comprising the additional step of sieving the porogen to a particle size of less than 300 microns.

* * * * *